United States Patent [19]

Inward

[11] Patent Number: 4,900,534
[45] Date of Patent: Feb. 13, 1990

[54] PREPARATION OF ANTIPERSPIRANTS

[75] Inventor: Peter W. Inward, Wirral, United Kingdom

[73] Assignee: Lever Brothers Company, New York, N.Y.

[21] Appl. No.: 82,024

[22] Filed: Aug. 5, 1987

[30] Foreign Application Priority Data

Aug. 11, 1986 [GB] United Kingdom ............... 8619553

[51] Int. Cl.$^4$ .................... C01B 9/02; C01B 9/04; C01B 9/06
[52] U.S. Cl. ...................................... 423/463; 424/66
[58] Field of Search ........................... 423/463; 424/66

[56] References Cited

U.S. PATENT DOCUMENTS

| | | | |
|---|---|---|---|
| 2,906,668 | 9/1959 | Beekman | 423/463 X |
| 3,792,068 | 2/1974 | Luedders | 260/429 |
| 3,947,556 | 3/1976 | Jones et al. | 423/463 |
| 4,359,456 | 11/1982 | Gosling | 424/68 |
| 4,435,382 | 3/1984 | Shin et al. | 424/66 |
| 4,605,554 | 8/1986 | Prussin et al. | 424/66 |

FOREIGN PATENT DOCUMENTS 1353916  5/1974  United Kingdom .
2144992A 3/1985  United Kingdom .

Primary Examiner—W. J. Shine
Attorney, Agent, or Firm—Gerard J. McGowan, Jr.

[57] ABSTRACT

The disclosure concerns a process for the manufacture of aluminium zirconium halohydrate having an aluminium:zirconium molar ratio of from 2:1 to 7:1 and having a metal:chlorine molar ratio of from 0.9:1 to 2.1:1. Metallic aluminium is dissolved in an aqueous starting solution comprising an oxyhalide, hydroxyhalide or carbonate of zirconium and an aluminium halide or basic aluminium halide, which solution is heated at about 50° C. to 105° C. The solution of the final aluminium zirconium halohydrate has a concentration of metal of 0.5 to 2.3 moles/kg and a size exclusion chromatogram of which the Band III proporition is at least 20%.

11 Claims, No Drawings

PREPARATION OF ANTIPERSPIRANTS

This invention relates to the preparation of antiperspirants, more particularly to processes for preparing aluminium zirconium halohydrates, especially aluminium zirconium chlorhydrates.

Processes for the preparation of aluminium zirconium chlorhydrates have been known for many years. U.S. Pat. No. 2,906,668 (Beekman) describes a process in which aluminium, a zirconyl compound and a basic aluminium chloride are interacted to form a gel which is heated until the gel liquefies and remains a liquid on cooling.

U.S. Pat. No. 3,792,068 (Luedders et al) describes a process wherein aluminium chlorhydroxide, zirconyl hydroxychloride and glycine are co-dried to form a powder.

GB-A No. 1 353 916 (Procter & Gamble) describes a process which involves heating a mixture of an aluminium chlorhydrate and zirconyl hydroxychloride at from about 88° C. to about 107° C. for from about 0.5 hour to 5 hours.

A number of aluminium zirconium chlorhydrates are commercially available, some of which also comprise a content of glycine. These have an aluminium:zirconium molar ratio within the range 2:1 to 7:1 and have a metal:chlorine ratio in the range 0.9:1 to 2.1:1. Examples of commercially available aluminium zirconium chlorhydrate, are the materials sold by the Reheis Chemical Co. under the REZAL trade name comprising REZALs 36G, 36 and 67, and the materials sold by Wickhen Products Inc. under the WICKENOL trade name comprising WICKENOLs 368, 669, 370, 372, 373 and 379.

Recently it has been suggested in GB-A No. 2 144 992 (Gillette) that aluminium zirconium chlorhydrates of enhanced antiperspirant efficacy can be made by a process which involves heating an aqueous solution of a mixture of an aluminium chlorhydrate and zirconyl hydroxychloride comprising 2 to 20% solids at a temperature of at least 50° C. to bring about certain changes in the distribution of the complexes present in the solution as indicated by a gel permeation chromatographic procedure described in the patent application.

At least so far as the process of the Gillette patent involves the heating of a relatively dilute solution of aluminium chlorhydrate it is similar to the process described in U.S. Pat. No. 4,359,456 (Gosling et al). The Gosling et al process is directed to the enhancement of the antiperspirant efficacy of, inter alia, aluninium chlorhydrate and involves the heat-treatment of relatively dilute solutions thereof. The heat treatment results in a modification of the distribution of the polymeric species and the modification is expressed as a function of the area of a band, called Band III, of a chromatogram obtained by a chromatographic analytical procedure described in the patent.

The present invention concerns a process for the direct preparation of aluminium zirconium halohydrates of enhanced efficacy.

According to the invention there is provided a process of making an aluminium zirconium halohydrate having an aluminium:zirconium molar ratio of from 2:1 to 7:1, preferably from 3:1 to 5:1, and having a metal:-chlorine molar ratio of from 0.9:1 to 2.1:1, preferably 1.3:1 to 1.9:1, which process comprises dissolving metallic aluminium in an aqueous starting solution of:

(i) zirconium oxyhalide, zirconium hydroxyhalide, zirconium carbonate or a mixture thereof; and
(ii) aluminium halide or a basic aluminium halide i.e. an aluminium halide of formula $Al_2 Hal_x (OH)_{6-x}$ where Hal is halogen (chlorine, bromine or iodine) and x is from 1 to 6 by heating the aqueous starting solution, which may initially form a gel, at about 50° C. to about 105° C. for a time just long enough to dissolve sufficient aluminium to produce an aqueous solution of a final aluminium zirconium halohydrate having an aluminium:zirconium molar ratio in the range 2:1 to 7:1 and a metal:halogen molar ratio of from 0.9:1 to 2.1:1, and the concentration of metal (aluminium and zirconium) in the starting solution and the amount of aluminium dissolved being such that the metal concentration in the solution of the final aluminium zirconium halohydrate is from 0.5 to 2.3 moles/kg and said final aluminium zirconium halohydrate having a size exclusion chromatogram of which the Band III proportion is at least 20%

A Band III proportion refers to the area of a particular band, referred to as Band III, of a chromatogram as a proportion of the sum of the areas of the bands as fully described hereinafter.

Optionally the process of the invention comprises the further step of drying the solution of the final aluminium zirconium halohydrate so as to give the aluminium zirconium halohydrate in the form of a hydrated powder having a Band III proportion of at least 20%.

An aluminium zirconium halohydrate glycine complex may be obtained by including glycine in the reaction medium, or by including it in the solution of the final aluminium zirconium halohydrate product prior to the optional drying.

Preferably the concentration of metal in the final aluminium zirconium halohydrate is from 0.5 to 2.0, more preferably from 1.0 to 1.5, moles/kg.

Preferably the Band III proportion is at least 25%, more desirably at least 30%.

Preferably the aluminium zirconium halohydrate is a chlorhydrate or bromhydrate.

Characterisation of materials containing species differing in size by means of size exclusion chromatography is generally known. The size exclusion chromatographic procedures for characterising the aluminium zirconium chlorhydrates of this invention will now be described.

The analytical procedure is performed on a stainless steel column of dimensions 25–30 cm high and of about 7 mm internal diameter packed with porous silica of nominal particle size 5 microns and pore size of 60 Angstroms, which silica has been deactivated by silylation to eliminate adsorption and unwanted ionic effects in size exclusion separations. A suitable silica is that available commercially as LiChrosorb RP-2. The silica employed by the Applicants in deriving analytical data given herein had a cumulative undersize particle size distribution by weight of 10% less than 5 microns, 50% less than 6 microns and 90% less than 7 microns.

The column is fitted at the bottom with a zero dead volume fitting containing a 2 micron mesh stainless steel bed support. The silica is packed into the column by the high pressure slurry method (see Practical High Performance Liquid Chromatography, Edited by C. F. Simpson, 1976, Appendix II), using dichloromethane as the packing medium.

After packing, the column is capped with another zero dead volume fitting containing a 2 micron stainless steel mesh. The packed column is then eluted with 200 ml of methanol at a flow rate of about 10 ml/min, using a high pressure pump, to consolidate the bed and wash out the packing medium.

A differential refractive index monitor (e.g. Waters R401) is used to detect sample fractions as they are eluted. It is linked to a pen recorder to provide a chromatogram and to an integrator which measures the elution times of the fractions and the relative chromatographic band areas. The integrator is required to measure areas of bands not resolved to the baseline by dropping perpendiculars from the lowest point of the valleys separating the bands to the baseline.

The column packing should be tested according to the procedure of Bristow & Knox (Chromatographia, Volume 10, No. 6, June 1977, pp 279-89) for reverse phase materials and should generate at least 20,000 plates/meter for the test component phenetole.

To prepare test solutions of the materials for analysis those already in solution are used undiluted unless the aluminium concentration exceeds 2.5% by weight in which case they are diluted with deionized water to give a solution containing 2.5% by weight aluminium. Solid materials (e.g. spray dried powders) are dissolved in deionized water to give a solution containing 2.5% by weight aluminium. Solids or solutions which do not disperse readily on shaking are dispersed by treatment in an ultrasonic bath (e.g. Sonicor Model No. SC-150-22TH) for 5 minutes. The solutions prepared in this way are filtered through a 25 mm diameter membrane having a pore size of 0.025 micrometers to give the test solutions. The preparation of a test solution is carried out immediately prior to application of a sample to the column.

A sample of the test solution containing about 2 to 4 micromoles of aluminium is applied to the top of the column by means of a precision micro-liter syringe and a sample injection port. The sample is eluted with a $1 \times 10^{-2}$ M aqueous nitric acid solution at a flow rate of 1.0 ml/min using a high pressure pump.

Eluted fractions of a test sample are characterised by means of the ratio of their retention times to the retention time of the totally included species. In the case of aluminium chlorhydrates and aluminium zirconium chlorhydrates the totally included species arises from hydrochloric acid (which is present in acidified solutions of these chlorhydrates) as can be shown by comparison of its retention time with that of a sample of hydrochloric acid. Using columns satisfying the above description and employing a standard solution of an aluminium chlorhydrate prepared as described below, the Applicants have obtained separation into four aluminium-containing fractions having relative retention times within the ranges indicated.

|  | Band I | Band II | Band III | Band IV |
|---|---|---|---|---|
| Relative Retention Time Range | 0.62-0.70 | 0.71-0.75 | 0.76-0.82 | 0.83-0.97 |

The standard aluminum chlorhydrate solution is prepared as a solution containing 12.5% by weight aluminium from 19.1 g of aluminium chloride hexahydrate, 10.5 g of 99.9% pure aluminium wire (0.76 mm diameter, cut in approximately 1 cm lengths and degreased by washing in acetone) and 70.4 g of deionised water. The mixture is stirred and heated at 80°-90° C. under a reflux condenser until all of the aluminium is dissolved. Any traces of insoluble solids are removed by filtration to give a clear solution.

When this material is analysed by the size exclusion chromatographic procedure described herein, there are obtained the following four fractions having typical relative retention times and chromatographic band areas expressed as percentages of the total chromatographic band area representing aluminium-containing material.

|  | Band I | Band II | Band III | Band IV |
|---|---|---|---|---|
| Relative Retention Time | 0.65 | 0.73 | 0.79 | 0.91 |
| Band Area % of total aluminium band area | 39 | 51 | 4 | 6 |

It will be appreciated by those skilled in the art that mechanisms of separation other than the principal mechanism of size exclusion may play a part in this type of chromatography. Examples of the processes would be adsorption effects and hydrodynamic effects. Thus although it is possible for a given column and constant operating conditions to lead to invariable relative retention times, minor variations in particle size range and pore size distribution of the column packing material may lead to slight differences in relative retention times.

It has been observed that the filtrate from the filtration through the 25 mm diameter membrane of a solution of an aluminium zirconium chlorhydrate contains most if not all of the aluminium of the original solution but may contain little of the zirconium. It has also been found that filtration causes only minor changes in the chromatogram even when most of the zirconium is removed on filtration. It is therefore deduced that much of the zirconium that is applied to the column is retained on the column. In cases where zirconium is eluted from the column it appears either in the first peak, which is generally very small, or with the chloride. For these reasons the chromatographic method described is best considered as SEC (size exclusion chromatography) of the aluminium-containing component of the aluminium zirconium chlorhydrate.

Consistent with this is the Applicant's finding that the relative retention times of the peaks arising from the chromatography of a series of aluminium zirconium chlorhydrates are virtually identical to the ranges reported above for the standard solution of aluminium chlorhydrate.

Aluminium zirconium halohydrates are characterised in this application by the proportion of the area of Band III of their size exclusion chromatogram expressed as a percentage of the sum of the areas of all the Bands except that corresponding to the included species. Thus the

| | Area of Band III |
|---|---|
| Band III proportion = 100 × | Sum of the areas of all the bands except that attributed to the included species. |

An essential feature of the process of the invention for making an aluminium zirconium halohydrate, particularly an aluminium zirconium chlorhydrate, in solution or powder form with high antiperspirant activity is the use of proportions of reactants such that when the desired product is formed, usually at the point when substantially all the aluminium has dissolved, the concentration of metal ions in the solution is relatively low and in the range of 0.5-2.3, preferably 0.5-2.0, moles/kg.

The reaction is most conveniently carried out at atmospheric pressure although elevated pressure for example, can be used. Within the ranges of operating conditions referred to above the formation of products having a relatively high Band III proportion is favoured by the choice of lower metal concentrations within the stated range e.g. 1.3 moles of metal per kg of solution and below. The lower limit is largely determined by practical considerations as solutions having a metal concentration below about 0.5 moles per kg of solution become inconveniently dilute for antiperspirant use or for subsequent spray-drying.

For a given final metal ion concentration, within the ranges specified, relatively minor influences are the temperature at which the reaction is conducted and the final aluminium:zirconium and metal ion:halide ratios.

The reaction may be carried out in the presence of glycine or other neutral amino-acid, or these may be added at the end of the reaction. At the appropriate concentration 2-10% w/w glycine is beneficial in helping to control gel formation in some reactions and appears to have only a minor effect on the Band III proportion. The reaction proceeds more smoothly in the presence of glycine but may be somewhat extended.

The form of the aluminium metal used in the reaction, particularly its fineness of division, also influences the rate of reaction. Generally it is preferred that extremely prolonged reactions should be avoided, as these may result in products containing insoluble material and some reduction in Band III proportion.

The powdered aluminium zirconium halohydrates produced in accordance with this invention as described above are particularly suitable for use in antiperspirant compositions, especially non-aerosol compositions, in which they are suspended in a carrier medium. A number of suitable carrier media for suspension-type antiperspirant compositions are disclosed in U.S. Pat. No. 4,359,456 (Gosling et al).

The following experiments illustrate the effect of various factors, e.g. final concentration and reaction time, on the Band III proportion of the reaction product.

EXPERIMENT 1

Aluminium chloride hexahydrate (7.2 g) and zirconyl chloride octahydrate, (22.4 g) were dissolved in water (214.5 g). This solution was placed in a conical flask fitted with a thermometer and an air condenser. A magnetic stirrer bar was added and the temperature raised to 90° C. with stirring on a magnetic stirrer-hotplate. Aluminium foil, BDH laboratory reagent grade 0.051 mm thick (5.9 g) was chopped up and added in portions. The first portion (1.0 g) was added during the warm-up stage and the remainder was added as quickly as was consistent with a controlled reaction, and maintenance of the temperature at 90°±5° C. The reaction was completed in 3 days. The reaction product was filtered to give a clear solution.

EXPERIMENT 2

Experiment 1 was repeated, using aluminium chloride hexahydrate (3.6 g), zirconyl chloride (11.2 g), water (232.3 g) and aluminium foil (3.0 g). The reaction was completed in 3 days.

EXPERIMENT 3

Experiment 1 was repeated using aluminium in the form of Alpoco 200/Dust, 99.7% pure. The reaction was completed in 3 hours.

EXPERIMENT 4

Aluminium chloride hexahydrate (14.4 g), zirconyl chloride octahydrate (44.8 g) and glycine (10 g) were dissolved in water (179.0 g). This solution was placed in a conical flask fitted with a thermometer and air condenser. A magnetic stirrer bar was added and the temperature raised to 90° C. with stirring on a magnetic stirrer-hotplate. Atomised aluminium powder (Alpoco 200/Dust) 99.7% pure, (11.9 g) was added in portions. The first portion (1 g) was added during the warm-up stage and the remainder was added as quickly as was consistent with a controlled reaction, and the maintenance of the temperature at 90°±5° C. The flask was cooled with water if necessary. The reaction was completed in 6 hours. The reaction mixture was filtered to give a clear solution.

EXPERIMENT 5

Experiment 4 was repeated using aluminium foil, save that the glycine was added during initial gel formation, 85 minutes after the warm-up had started. The reaction was completed in 5 days.

EXPERIMENT 6

Experiment 4 was repeated using 169 g of water. The reaction was completed in 4 hours 10 minutes.

EXPERIMENT 7

Experiment 4 was repeated using aluminium chloride hexahydrate (7.2 g), zirconyl chloride octahydrate (22.4 g), glycine (5.0 g), water (209.5 g) and aluminium powder (5.9 g). The reaction was completed in 4 hours.

EXPERIMENT 8

Aluminium chlorhydrate (ACH) in approximately 50% solution containing 12.25% w/w aluminium (78.7 g) was mixed with water (122.7 g) and zirconyl chloride octahydrate (44.8 g) was dissolved in this mixture. This solution was placed in a conical flask fitted with a thermometer and an air condenser. A magnetic stirrer bar was added and the temperature raised to 90° C. with stirring on a magnetic stirrer-hotplate. Chopped aluminium foil (3.9 g) was added in portions. The first portion (0.4 g) was added during the warm-up stage and the remainder was added as quickly as was consistent with a controlled reaction, and maintenance of the temperature at 90°±5° C. The reaction was completed in 3 days. The reaction mixture was filtered to give a clear solution.

EXPERIMENT 9

Experiment 8 was repeated using Alpoco 200/Dust, 99.7% pure. The reaction was completed in 5 hours 15 minutes.

EXPERIMENT 10

Aluminium chlorhydrate in approximately 50% solution containing 12.25% w/w aluminium (39.4 g) was dissolved in water (136.3 g). The solution was placed in a conical flask fitted with a thermometer and air condenser. A magnetic stirrer bar was added. Zirconyl chloride octahydrate (22.4 g) was dissolved in water (50 g) and this solution was placed in a separating funnel set to run into the top of the condenser. The temperature of the conical flask was raised with stirring to 90° C. on a magnetic stirrer-hotplate. Chopped aluminium foil (1.9 g) was added in portions. The first portion (0.4 g) of the aluminium and the first 10 ml of the zirconyl chloride solution was added during the warm-up stage and the remainder of these was added as quickly as was consistent with a controlled reaction, and maintenance of the temperature at 90°±5° C. The flask was cooled with water if necessary. The reaction was completed in 2 days. The reaction mixture was filtered to give a clear solution.

EXPERIMENT 11

Aluminium chlorhydrate in approximately 50% solution containing 12.25% w/w aluminium (39.4 g) and zirconyl chloride octahydrate (22.4 g) were dissolved in water (186.3 g). The solution was placed in a conical flask fitted with a thermometer and air condenser. A magnetic stirrer bar was added, and the temperature raised to 90° C. with stirring on a magnetic stirrer-hotplate. Atomised aluminium powder (Alpoco 200/Dust) 99.7% pure (1.9 g) was added in portions. The first portion (0.2 g) was added during the warm-up stage and the remainder was added as quickly as was consistent with a controlled reaction, and maintenance of the temperature at 90° C.±5° C. The reaction was complete in 4 hours 20 minutes.

EXPERIMENT 12

Experiment 11 was repeated but adding 5.0 g glycine to the initial solution in place of 5.0 g of the water. The reaction was completed in 4 hours 10 minutes. The reaction mixture was filtered to give a clear solution.

EXPERIMENT 13

Experiment 8 was repeated but replacing 10 g of the water by glycine (10.0 g) and using Alpoco 200/Dust, 99.7% pure. The reaction was completed in 4 hours 15 minutes.

The above experiments are summarised in the following Table which also gives the Band III proportions for the respective products.

solving metallic aluminium in an aqueous starting solution of:
  (i) zirconium oxyhalide, zirconium hydroxyhalide, zirconium carbonate or a mixture thereof, and
  (ii) aluminium halide or a basic aluminium halide of formula $Al_2 Hal_x (OH)_{6-x}$ where Hal is halogen of chlorine, bromine or iodine and x is from 1 to 6,
by heating the aqueous starting solution at about 50° C. to about 105° C. for a time just long enough to dissolve sufficient aluminium to produce an aqueous solution of a final aluminium zirconium halohydrate having an aluminium:zirconium molar ratio in the range 2:1 to 7:1 and a metal:halogen molar ratio of from 0.9:1 to 2.1:1, and the concentration of metal (aluminium and zirconium) in the starting solution and the amount of aluminium dissolved being such that the metal concentration in the solution of the final aluminium zirconium halohydrate is from 0.5 to 1.5 moles/kg and said final aluminium zirconium halohydrate having a size exclusion chromatogram of which the Band III proportion is at least 20%.

2. Process as claimed in claim 1 wherein the aluminium zirconium halohydrate has an aluminium:zirconium molar ratio of from 3:1 to 5:1.

3. Process as claimed in claim 1 wherein the aluminium zirconium halohydrate has a metal:chlorine molar ratio of 1.3:1 to 1.9:1.

4. Process as claimed in claim 1 comprising the further step of drying the solution of the final aluminium zirconium halohydrate so as to give the aluminium zirconium halohydrate in the form of a hydrated powder having a Band III proportion of at least 20%.

5. Process as claimed in claim 1 wherein the concentration of metal in the final aluminium zirconium halohydrate is from 1.0 to 1.5 moles/kg.

6. Process as claimed in claim 1 wherein the Band III proportion is at least 25%.

7. Process as claimed in claim 4 wherein the Band III proportion is at least 25%.

8. Process as claimed in claim 6 wherein the Band III proportion is at least 30%.

9. Process as claimed in claim 7 wherein the Band III proportion is at least 30%.

10. Process as claimed in claim 1 wherein the aluminium zirconium halohydrate is an aluminium zirconium chlorhydrate.

11. Process as claimed in claim 1 wherein the aluminium zirconium halohydrate is an aluminium zirconium bromhydrate.

TABLE I

| Experiment No | Final Metal concentration Moles/kg | Form of Al | Reaction Time | Band III Proportion (%) |
|---|---|---|---|---|
| Reaction Al + AlCl₃ + ZrOCl₂ | | | | |
| 1 | 1.28 | Foil | 3 days | 31 |
| 2 | 0.64 | Foil | 3 days | 52 |
| 3 | 1.28 | Powder | 3 hours | 45 |
| Reaction Al + AlCl₃ + ZrOCl₂ + glycine | | | | |
| 4 | 2.55 | Powder | 6 hours | 21 |
| 5 | 2.55 | Foil | 5 days | 9 |
| 6 | 2.55 | Powder | 4.17 hours | 23 |
| 7 | 1.28 | Powder | 4 hours | 42 |
| Reaction Al + ACH + ZrOCl₂ | | | | |
| 8 | 2.55 | Foil | 3 days | 10 |
| 9 | 2.55 | Powder | 5.25 hours | 16 |
| 10 | 1.28 | Foil | 2 days | 31 |
| 11 | 1.28 | Powder | 4.33 hours | 48 |
| Reaction Al + ACH + ZrOCl₂ + glycine | | | | |
| 12 | 1.28 | Powder | 4.17 hours | 39 |
| 13 | 2.55 | Powder | 4.25 hours | 12 |

Note: All the reactions were conducted at 90° C. to give a product having an aluminum:zirconium molar ratio of 3.6 and a metal:chlorine molar ratio of 1.4.

What is claimed is:

1. Process of making an aluminium zirconium halohydrate having an aluminium:zirconium molar ratio of from 2:1 to 7:1 and having a metal:halogen molar ratio of from 0.9:1 to 2.1:1, which process comprises dis-

* * * * *